United States Patent [19]

Dahrendorf et al.

[11] Patent Number: 4,984,476
[45] Date of Patent: Jan. 15, 1991

[54] AIR CONVEYOR FOR GAS-SAMPLING TUBES

[75] Inventors: Klaus D. Dahrendorf; Ulrich Noack, both of Berlin, Fed. Rep. of Germany

[73] Assignee: Auergesellschaft GmbH, Fed. Rep. of Germany

[21] Appl. No.: 423,937

[22] Filed: Oct. 19, 1989

[30] Foreign Application Priority Data

Oct. 21, 1988 [DE] Fed. Rep. of Germany ....... 3835885

[51] Int. Cl.$^5$ .............................................. G01N 1/24
[52] U.S. Cl. ................................ 73/864.35; 73/31.02; 73/864.73
[58] Field of Search ........... 73/864.34, 864.35, 864.73, 73/864.74, 863.71, 863.72, 863.73, 23, 28, 29, 31.02, 31.01, 31.03, 23.2

[56] References Cited

U.S. PATENT DOCUMENTS

| | | | |
|---|---|---|---|
| 3,422,681 | 1/1969 | Sanders | 73/864.34 |
| 3,446,600 | 5/1969 | Wächter et al. | 73/864.34 X |
| 3,482,451 | 12/1969 | Hidina | 73/864.34 |
| 3,759,106 | 9/1973 | Wächter et al. | 73/864.34 |
| 3,861,217 | 1/1975 | Rabenecker et al. | 73/864.34 |
| 4,159,942 | 7/1979 | Greer et al. | 378/47 X |
| 4,522,056 | 6/1985 | Chin et al. | 73/64.2 |
| 4,574,647 | 3/1986 | Molt | 73/864.34 |
| 4,793,706 | 12/1988 | Csillag et al. | 356/335 |

FOREIGN PATENT DOCUMENTS

| | | | |
|---|---|---|---|
| 3330578 | 3/1985 | Fed. Rep. of Germany ... | 73/864.34 |
| 887995 | 12/1981 | U.S.S.R. | 73/864.34 |

*Primary Examiner*—Tom Noland
*Attorney, Agent, or Firm*—Reed Smith Shaw and McClay

[57] ABSTRACT

An air conveyor for a gas-sampling tube that is used for detecting foreign gases or suspended substances in air is described. The air conveyor comprises a body, serving as a handle, that has a control rod which is guided and lockable in a through-duct therein, and which is connected at one end to a bellows that serves as a suction element. The beginning and the end of the suction stroke is uniquely determined by a locking and releasing mechanism connected to the control rod thereby ensuring an exactly reproducible stroke volume. The locking and releasing mechanism utilizes two lever-like linkages, each provided with a hook, which are pivotally disposed in the body one under the other and parallel to the control rod. The free end of the control rod has at least one recess which is in operative connection with the hook on the first lever to secure the control rod in position at the beginning of a suction stroke and with the hook on the second lever to secure the control rod in position at the end of the suction stroke.

10 Claims, 3 Drawing Sheets

AIR CONVEYOR FOR GAS-SAMPLING TUBES

FIELD OF THE INVENTION

The present invention relates to an air conveyor for a gas sampling tube that is used for detecting foreign gases or substances suspended in air.

BACKGROUND OF THE INVENTION

An air conveyor for a sampling tube is disclosed in German Patent No. DE 333057 C2. In this device, a spring-loaded counting ring is disposed around the axis of the body and, by rotation, unlocks the control rod for releasing the suction stroke of the bellows. The control rod is locked in the body in both end positions by means of a radially extending spring-loaded stop cam disposed in the control rod. Depending upon the end position taken up, the spring-loaded stop cam engages in radial locking recesses in the wall of the body or, in the case of the end position when the bellows is vented, it cooperates with a spring-loaded locking element disposed under the counting ring. This device, however, may result in disadvantageous inaccuracies in determining the beginning and the end of the suction stroke due to the inaccuracies in stopping the control rod.

It would be desirable, therefore, to develop an air conveyor wherein the beginning and the end of the suction stroke is uniquely determined by an improved locking and releasing mechanism thereby ensuring an exactly reproducible stroke volume.

SUMMARY OF THE INVENTION

Generally, the present invention provides an air conveyor for a gas-sampling tube used for detecting foreign material suspended in air comprising: a body serving as a handle; a control rod having a free end, guided and lockable in a through-duct running through the body; the control rod connected opposite the free end to a piston of a suction bellows, the bellows including an air outlet valve in the piston; a sealing insert disposed at an end of the body opposite the bellows for receiving the gas-sampling tube; and a locking and releasing comprising: (a) two lever linkages, each provided with a hook, which are pivotally disposed in the body one under the other and parallel to the control rod; and (b) the free end of the control rod having at least one recess therein that is in operative connection with at least one hook of the lever linkages for lockably securing the control rod in position at the beginning and at the end of a suction stroke, the control rod being releaseable to initiate the suction stroke of the bellows by pressing a push-button connected to one of the linkages.

The locking and releasing mechanism preferably uses two lever-like linkages, each provided with a hook that operates in a recess on the free end of the control rod to lock and secure the control rod at the start (aeration) and finish (ventilation) position of the suction stroke. The linkage levers are contained in a subassembly with a push-button intricately formed on the first lever. To initiate the suction stroke of the bellows, the first lever is pushed thereby releasing the hook on the first lever from engagement with the recess on the control rod. After initiating the suction stroke, the unlocked and released control rod, with the bellows, carries out a suction stroke and draws a predefined test volume of air through a gas-sampling tube and into the air conveyor. The predetermined end of the suction stroke is reached when the hook of the second lever engages recess on the control rod, thereby locking it into the finish position.

One advantage of the present invention is that the locking and releasing mechanism for the suction element is combined in a subassembly and generates the same suction characteristic for each suction stroke, thereby, increasing the accuracy of each measurement. Other details, objects and advantages of the present invention will become more readily apparent from the following description of the presently preferred embodiment thereof.

BRIEF DESCRIPTION OF THE INVENTION

In the accompanying drawings, a preferred embodiment of the present invention is illustrated by way of example only, wherein.

DESCRIPTION OF THE PREFERRED EMBODIMENT

Figure 1:
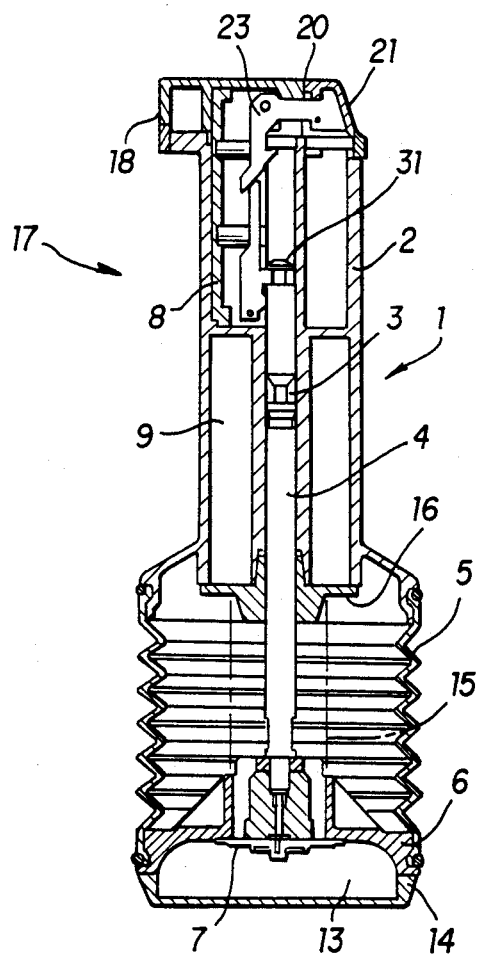
FIG. 1 is a longitudinal section through the air conveyor when the bellows is aerated (i.e. the air conveyor is relieved from pressure at the end of a suction stroke)
Figure 2:
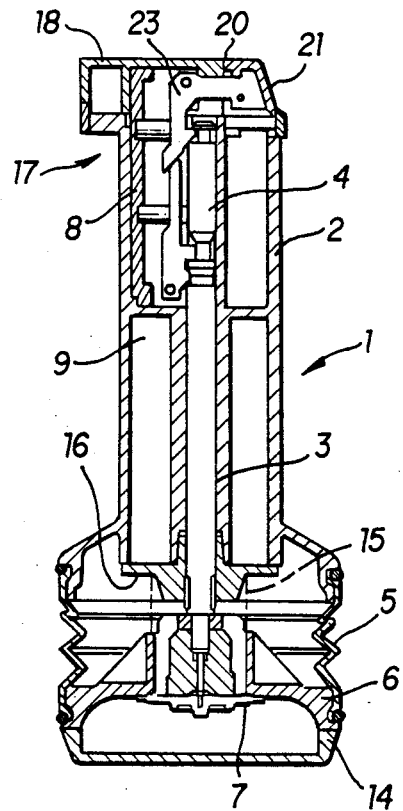
FIG. 2 is a longitudinal section through the air conveyor when the bellows is vented (i.e. the air conveyor is under pressure at the beginning of a suction stroke)

As FIGS. 1 and 2 show, the air conveyor 1 substantially comprises: a body 2 having a concentric through-duct 3; a control rod 4 that is positively or slideably guided in the through-duct 3; a suction element preferably in the form of a bellows 5; a piston 6 firmly connected to the control rod; an air outlet valve 7 disposed on the piston 6; and a locking and releasing mechanism 8 for locking and releasing the control rod 4. The bellows 5 shown in FIG. 1 is at the end of the suction stroke (aeration). The bellows 5 shown in FIG. 2 is at the beginning of the suction stroke (ventilation).

Figure 3:
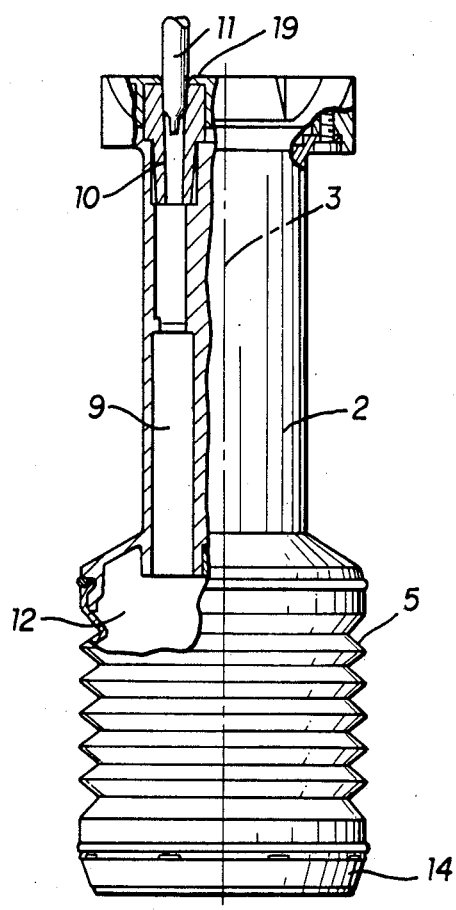
FIG. 3 is a partial longitudinal section through the air conveyor near the gas duct.

Referring to FIG. 3, a gas duct 9 extends parallel to the through-duct 3 and eccentrically with respect to the body 2 and over the entire length thereof. At one end of gas duct 9, a sealing insert 10 of elastomeric material is placed for receiving the gas-sampling tube 11 when it is inserted into the gas duct 9. The other end of gas duct 9 is connected to the interior 12 of the bellows 5. In this manner, the gas under investigation is sucked through the gas-sampling tube 11 by the bellows 5 which acts as a suction element.

The bellows 5 is made of elastomeric material and is permanently screwed at one end to the body 2 and at the other end to the piston 6 that is connected to the control rod 4. The air outlet valve 7 is disposed on the outside of the piston 6, which constitutes a cavity 13, and is in operative connection for flow purposes with the interior 12 of the bellows 5. The air outlet valve 7 is for blowing out air when the bellows 5 is compressed and is closed during the suction stroke of the bellows 5. The cavity 13 in the piston 6 is closed by a cover 14. Inside the bellows 5, a cylindrical compression spring 15 extends around the control rod 4 and abuts the piston 6 and the opposite end face 16 of the body 2. The bellows 5 preferably is circular in cross-section and substantially equal in diameter to the body 2 screwed onto the bellows 5.

Figure 4:
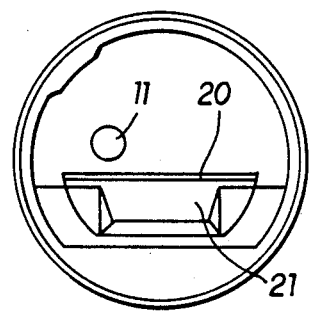
FIG. 4 is a plan view of the air conveyor.

Above the bellows 5, the body 2 is constructed as a handle member for gripping with a hand, and a headpiece 17 serving as a closure is integrally moulded and contains the locking and releasing mechanism 8 for the control rod 4. A cap 18 serving as a closure member is non-releaseably disposed above the headpiece 17. The cap 18 is formed with an opening 19 corresponding to the sealing insert 10 that receives the gas-sampling tube 11 (see FIGS. 3 and 4), and a notch 20 for receiving a push-button 21 (reference FIG. 1, 2, and 4). The push-button 21 is a component of the locking and releasing mechanism 8.

Figure 8:
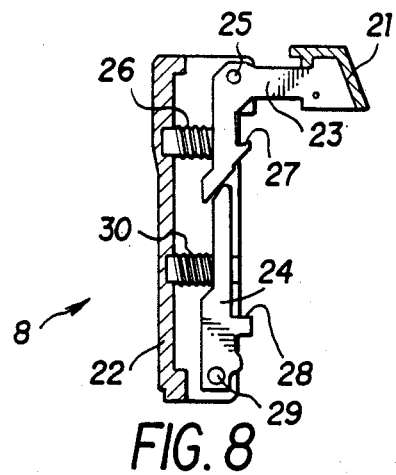
FIG. 8 is a section taken through the locking and releasing mechanism of FIG. 5.

As particularly shown in FIG. 8, the locking and releasing mechanism 8 comprises an insertion member 22 that carries an angular stop lever 23 and a rodlike rocking lever 24, the two cooperating with the control rod 4 in the process of aerating and venting the bellows 5 and releasing the control rod 4 from a starting position and locking it in the start and finish positions. The angular stop lever 23 is secured by a pin 25 in the insertion member 22 so as to be rotatable against the action of a spring 26. The end of the stop lever 23 projecting from the insertion member 22 comprises the push-button 21, whereas the other end carries an outwardly projecting hook 27. The rod like rocking lever 24 is disposed in the direction of its longitudinal axis vertically under the stop lever 23, and its bottom end is secured by a pin 29 in the insertion member 22 so as to be rotatable against the force of a spring 30. The free end of the rocking lever 24 is in operating contact with that end of the stop lever 23 which carries the hook 27. The rocking lever 24 has a hook 28 projecting outwardly from the insertion member 22. When the cap 18 is removed from the headpiece 17, the locking and releasing mechanism 8 is firmly inserted into the headpiece 17 and partly into the body 2 whereupon the hooked parts 27 and 28 of the rotatably mounted stop and rocking levers 23 and 24 come into operative contact with the control rod 4, which is guided by sliding in the through-duct 3.

Figures 5, 6, 7:
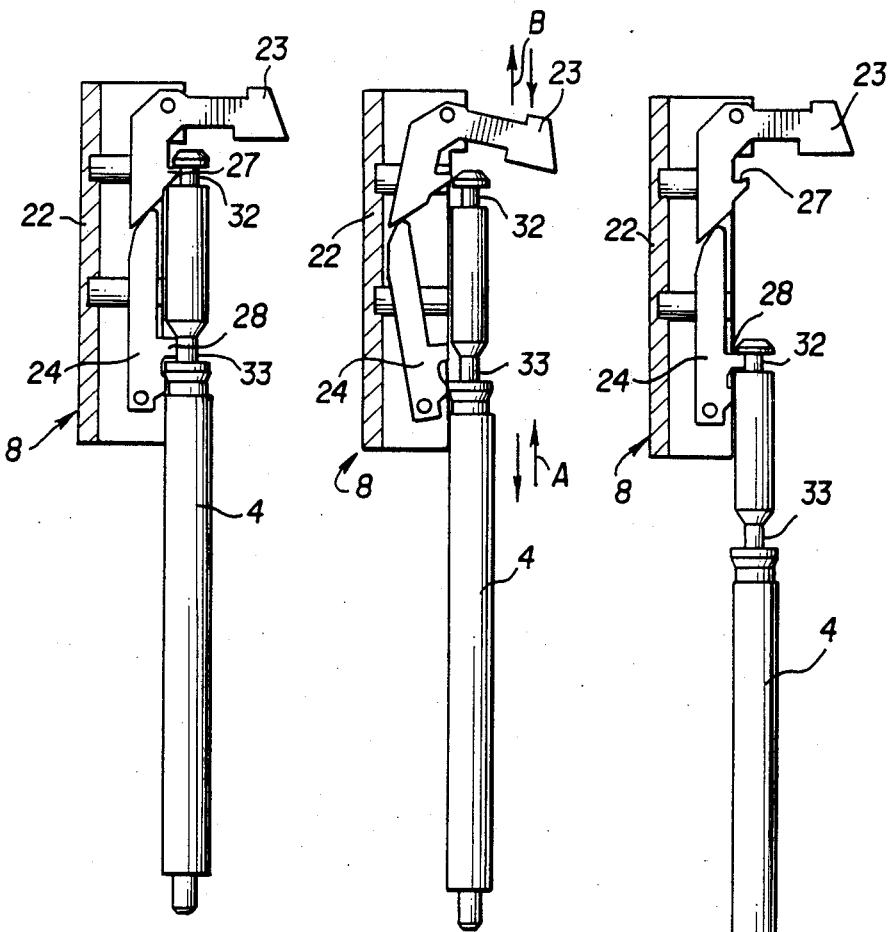
FIG. 5 is a side view of the control rod and the locking and releasing mechanism of the air conveyor shown in FIG. 2 when locked at the beginning of a suction stroke.
FIG. 6 shows the control rod of FIG. 5 being released for the carrying out a suction stroke.
FIG. 7 is a view of the control rod of FIG. 6 when it is locked at the end of a suction stroke.

The control rod 4 has a recess 32 at its free end 31 and a chamfered second recess 33 at a preset distance from the first recess. When the bellows is aerated and vented, the two recesses cooperate with the locking and releasing mechanism 8 to ensure accurate operation for fixing the beginning and end positions of the control rod 4. When the bellows 5 is fully aerated (FIG. 1), the hook 28 of the rocking lever 24 engages in the recess 32 of the control rod 4 and holds it in the locked position corresponding to the end of the suction stroke of the air conveyor 1 (FIG. 7). When the bellows 5 is vented (FIG. 2), the hook 27 of the stop lever 23 engages in the recess 32 of the control rod 4 and holds it in the locked position corresponding to the beginning of the suction stroke of the air conveyor 1 (FIG. 5). The alternate engagement of the hooks 27 and 28 of the two levers 23 and 24 of the locking and releasing mechanism 8 in the recess 32 characterizes the two respective positions for aeration and ventilation, that is, the beginning and end positions of the suction stroke of the air conveyor 1.

The second recess 33 in control rod 4 serves as a receiving chamber for the hook 28 of the rocking lever 24 projecting from the locking and releasing mechanism 8 at the beginning of the suction stroke when the rocking lever 24 is not used for locking the control rod 4, but locking is brought about by the hook 27 of the stop lever 23 engaging in the recess 32 of the control rod 4 (FIG. 5).

The following is a description of the sequence of operations of the air conveyor 1 for a gas-sampling tube 11. FIGS. 5, 6, and 7 show the manner of operation of the locking and releasing mechanism 8 and the control rod 4 (a) at the beginning of the suction stoke when the air conveyor 1 is pressurized (FIG. 5); (b) in the released position for performing the suction stroke (FIG. 6); and (c) at the end of the suction stroke when the air conveyor is depressurized (FIG. 7).

In the position at the end of the suction stroke of the air conveyor 1, the bellows is fully aerated (FIGS. 1, 3, and 7). A gas-sampling tube 11 is inserted into the sealing insert 10 (FIG. 3). The handle-shaped body 2 is taken in the operator's hand and the cover 14 of the piston 6 connected to the bellows 5 and the compression spring 15 are pressed against a solid object such as the operator's thigh whereupon the air in the bellows 5 escapes through the outlet valve 7 into the cavity 13, thus venting the bellows 5. Thereupon, the body 2 and the locking and releasing mechanism 8 move against the action of the spring 15 in the bellows 5, downwards along the control rod that slides in the through duct 3, until the spring-loaded hook 27 of the stop lever 23 in the locking and releasing mechanism 8 nonreleaseably engages in the recess 32 of the control rod 4 and thus determines the exact end position for complete venting of the bellows 5 and thereby ensures that the amount of air conveyed by suction into the air conveyor 1 is always the same during each operating stroke. Each completed suction stroke must always correspond to the complete suction volume of the completely vented bellows 5 so that the volume of gas sucked through the gas-sampling tube is always exact and reproducible.

The suction stroke of the bellows 5 is initiated by pressing the push-button 21, whereupon the hook 27 of the stop lever 23 moves out of the recess 32 in the control rod 4 that compresses the spring 15, so that the control rod is unlocked and released and, with the bellows 5, carries out a suction stroke and draws a predefined test volume of air through the gas-sampling tube 11, which is mounted in a fixed position in the air conveyor. During the suction process, the push-button is preferably held in the bottom position and is released only at the end of the suction stroke when the hook 28 of the rocking lever 24 engages in the recess 32 of the control rod 4 and thus locks it. The spring-mounted push-button jumps up, so that the end of the suction stroke can abruptly be seen and felt.

-g
While a presently preferred embodiment of practicing the invention has been shown and described with particularity in connection with the accompanying drawings, the invention may otherwise be embodied within the scope of the following claims.

What is claimed is:

1. An air conveyor for a gas-sampling tube used for detecting foreign material suspended in air comprising: a body serving as a handle; a control rod having a free end, guided and lockable in a through-duct running through the body; the control rod connected opposite the free end to a piston of a suction bellows, the bellows including an air outlet valve in the piston; a sealing insert disposed at an end of the body opposite the bellows for receiving the gas-sampling tube; and a locking and releasing mechanism comprising:
(a) two lever linkages, each provided with a hook, which are pivotally disposed in the body one under the other and parallel to the control rod; and
(b) the free end of the control rod having at least one recess therein that is in operative connection with at least one hook of the lever linkages for lockably securing the control rod in position at the beginning and at the end of a suction stroke, the control rod being releaseable to initiate the suction stroke of the bellows by pressing a push-button connected to one of the linkages.

2. An air conveyor as described in claim 1 wherein the two lever linkages comprise an angular lever integrally formed with the push-button and a rod lever, the two levers constituting a subassembly which is rotatable and pivotable in an insertion member.

3. An air conveyor as described in claim 2 wherein the angular lever is secured by a pin so as to be rotatable in the insertion member against the force of a first spring, and an end of the angular lever projecting from the insertion member is the push-button whereas the other end comprises the hook and which is outwardly projecting from the insertion member.

4. An air conveyor as described in claim 3 wherein the rod lever is disposed in the direction of its longitudinal axis under the angular lever, a bottom end of the rod lever is rotatably secured by a pin in the insertion member so as to be rotatable against the force of a second spring, an end of the rod lever opposite the bottom being in operative contact with an end of the angular lever and forming a hook which is outwardly projecting from the insertion member.

5. An air conveyor as described in claim 4 wherein a headpiece serving as a closure is integrally formed above the body and the insertion member containing the locking and releasing mechanism is insertable into the headpiece.

6. An air conveyor as described in claim 5 wherein a cap is disposed above the headpiece such that the cap is formed with an opening corresponding to the sealing insert for receiving the gas-sampling tube and is also formed with a notch for receiving the push-button.

7. An air conveyor as described in claim 4, wherein the control rod is formed with a second recess at a preset distance from the first recess for locking the control rod, when the bellows is vented, such that the hook of the rod lever is disposed in the second recess.

8. An air conveyor as described in claim 4 wherein the positions for aerating and venting the bellows are determined by alternate engagement of the hooks of the angular lever and the hook of the rod lever, respectively, in the first recess in the control rod.

9. An air conveyor as described in claim 1 wherein a gas duct extends parallel to the through-duct and eccentrically in the body and over the entire length thereof, and at one end has a sealing insert of elastomeric material for receiving the gas sampling tube whereas its other end is connected to a chamber inside the bellows.

10. An air conveyor as described in claim 1 wherein the push-button returns to its original position at the completion of the suction stroke.

* * * * *